United States Patent
Zhang (10) Patent No.: US 12,184,981 B2
(45) Date of Patent: Dec. 31, 2024

(54) OPTICAL SYSTEM FOR REAL-TIME CLOSED-LOOP CONTROL OF FUNDUS CAMERA AND IMPLEMENTATION METHOD THEREFOR

(71) Applicant: ROBOTRAK TECHNOLOGIES CO., LTD., Nanjing (CN)

(72) Inventor: Jie Zhang, Nanjing (CN)

(73) Assignee: ROBOTRAK TECHNOLOGIES CO., LTD., Nanjing (CN)

( * ) Notice: Subject to any disclaimer, the term of this patent is extended or adjusted under 35 U.S.C. 154(b) by 721 days.

(21) Appl. No.: 17/428,159

(22) PCT Filed: Jul. 9, 2019

(86) PCT No.: PCT/CN2019/095189
§ 371 (c)(1),
(2) Date: Aug. 3, 2021

(87) PCT Pub. No.: WO2020/258374
PCT Pub. Date: Dec. 30, 2020

(65) Prior Publication Data
US 2022/0060634 A1    Feb. 24, 2022

(30) Foreign Application Priority Data
Jun. 28, 2019  (CN) .......................... 201910578671.9

(51) Int. Cl.
*H04N 23/695* (2023.01)
*A61B 3/12* (2006.01)
(Continued)

(52) U.S. Cl.
CPC ............. *H04N 23/695* (2023.01); *A61B 3/12* (2013.01); *A61B 3/14* (2013.01); *G02B 26/101* (2013.01); *H04N 23/66* (2023.01)

(58) Field of Classification Search
CPC ........ H04N 23/695; H04N 23/66; A61B 3/12; A61B 3/14; A61B 3/1025; A61B 3/113;
(Continued)

(56) References Cited

U.S. PATENT DOCUMENTS

| | | | |
|---|---|---|---|
| 4,856,891 A | * | 8/1989 | Pflibsen ................. A61B 3/113 351/220 |
| 2012/0002029 A1 | * | 1/2012 | Sieracki ............. G01N 21/6456 348/79 |

(Continued)

FOREIGN PATENT DOCUMENTS

| | | |
|---|---|---|
| CN | 103961058 A | 8/2014 |
| CN | 104116495 B | 2/2016 |

(Continued)

OTHER PUBLICATIONS

International Search Report and Written Opinion issued for WO2020258374.

*Primary Examiner* — Travis S Fissel
(74) *Attorney, Agent, or Firm* — Bayes PLLC (57) ABSTRACT

An optical system for real-time closed-loop control of a fundus camera and an implementation method therefor. The optical system comprises an optical path structure composed of a fundus camera, light sources (LS1, LS2), a plurality of lenses (L1, L2, L2', L3') and a dividing mirror (DM1, DM2), and further comprises an orthogonal steering mirror group, which comprises: a first steering mirror (SM1) moving in a horizontal direction and a second steering mirror (SM2) moving in a vertical direction. The optical system converts fundus motion information obtained from a fundus camera image to residual motion information compensated by means of the first steering mirror (SM1) and the second steering mirror (SM2), uses a relationship between control parameters, and by means of a translation control instruction or/and the fundus rotation control instruction, operates the (Continued)

first steering mirror (SM1) and the second steering mirror (SM2) in real time to compensate for translational motion or/and controls the fundus camera to compensate for fundus rotation. By using the optical system and the implementation method therefor, and by improving the optical system of the fundus camera, the optical system is enabled to have a real-time closed-loop control function so as to implement real-time optical tracking of a fundus/retina position and a target.

11 Claims, 4 Drawing Sheets (51) Int. Cl.
*A61B 3/14* (2006.01)
*G02B 26/10* (2006.01)
*H04N 23/66* (2023.01)

(58) Field of Classification Search
CPC ....... A61B 3/102; A61B 3/0025; A61B 3/117; A61B 3/1173; A61B 3/163; A61B 5/163; A61B 5/1114; A61B 2034/2065; A61B 2017/00694; G02B 26/101; G02B 27/642
USPC .......................................... 351/206, 209–211
See application file for complete search history.

(56) References Cited

U.S. PATENT DOCUMENTS

| | | |
|---|---|---|
| 2016/0345828 A1 | 12/2016 | Yang et al. |
| 2017/0027441 A1 | 2/2017 | Larsen |

FOREIGN PATENT DOCUMENTS

| | | |
|---|---|---|
| CN | 107224268 A | 10/2017 |
| CN | 109924942 A | 6/2019 |
| CN | 109924943 A | 6/2019 |

* cited by examiner

OPTICAL SYSTEM FOR REAL-TIME CLOSED-LOOP CONTROL OF FUNDUS CAMERA AND IMPLEMENTATION METHOD THEREFOR

RELATED APPLICATIONS

This application is a U.S. national phase entry of and claims priority to PCT International Phase Application No. PCT/CN2019/095189, filed Jul. 9, 2019, which claims priority to Chinese Patent Application No. CN 201910578671.9, filed Jun. 28, 2019. The entire contents of the above-referenced applications and of all priority documents referenced in the Application Data Sheet filed herewith are hereby incorporated by reference for all purposes.

FIELD OF THE INVENTION

The present invention relates to fundus target tracking and imaging technology in the medical field, and in particular, to an optical system for real-time closed-loop control of a fundus camera and an implementation method therefor.

BACKGROUND

A fundus camera is an eyeball base inspection tool commonly used to observe the retina, optic disc, fundus capillary distribution, and the like. The fundus camera may be used medically to screen the optic nerve, retina, choroid, and refractive media of the fundus for disease. At the same time, the fundus camera may also assist in the diagnosis and condition judgment of other diseases, such as screen a retinal image to detect cerebral infarction, cerebral hemorrhage, cerebral arteriosclerosis, cerebral tumor, diabetes, nephropathy, hypertension, retinopathy of prematurity, glaucoma, macular degeneration, and the like. The sooner these diseases are detected, the more beneficial it is for clinical treatment. Therefore, the fundus camera is an indispensable medical device for clinical screening of fundus diseases.

However, the existing fundus camera usually does not have a real-time closed-loop control function, and thus cannot well support real-time optical tracking of the fundus position. Therefore, when using the fundus camera to obtain fundus position information to control another device to operate on the same fundus position, for example, to control optical coherence tomography (OCT) to scan the same fundus position or to control the laser strike position of laser surgery, due to a motion of an eyeball and fundus (retina), it is difficult to accurately and real-time control a spatial position of a light of the device on the fundus.

SUMMARY OF THE INVENTION

In view of this, the main objective of the present invention is to provide an optical system for real-time closed-loop control of a fundus camera and an implementation method therefor, which intend to improve the optical system for the fundus camera so that it has a real-time closed-loop control function to achieve real-time optically tracking of fundus/retina position and target.

To achieve the above objective, the technical solution of the present invention is as follows:

An optical system for real-time closed-loop control of a fundus camera comprises an optical path structure composed of a fundus camera, a light source, a plurality of lenses, and a dividing mirror, and further comprises an orthogonal steering mirror group, the orthogonal steering mirror group comprising a first steering mirror SM1 moving in a horizontal direction and a second steering mirror SM2 moving in a vertical direction; the optical system converting fundus motion information obtained from an image of the fundus camera into residual motion information that has been compensated by the SM1 and SM2, and manipulating the SM1 and SM2 respectively in real time to compensate for a translational motion or/and control the fundus camera to compensate for a fundus rotation by a translation control instruction and a fundus rotation control instruction using a relationship between control parameters.

The relationship between the control parameters is expressed by equation (1):

$$(x_{t+1}, y_{t+1}, \theta_{t+1}) = (x_t, y_t, \theta_t) + g(\Delta x_t, \Delta y_t, \Delta \theta_t) \quad (1)$$

wherein $(x_t, y_t)$ is the translation control instruction accumulated on the first steering mirror SM1 and the second steering mirror SM2 at a current time point, $\theta_t$ is the fundus/retinal rotation control instruction accumulated at the current time point; $(\Delta x_t, \Delta y_t)$ is a residual fundus translation amount obtained from the image of the fundus camera, $\Delta \theta_t$ is a residual fundus rotation amount obtained from the image; $(x_{t+1}, y_{t+1})$ is the translation control instruction that needs to be updated for the SM1 and SM2 at a next sampling time point, $\theta_{t+1}$ is the fundus/retinal rotation control instruction that needs to be updated at the next sampling time point; index t represents a time sequence; g is a gain of the closed-loop control system.

The control instructions for controlling the SM1 and SM2 are configured to be sent from a personal computer or a dedicated processor connected to the fundus camera of the optical system.

The SM1 and SM2 are a 6210H biaxial scanning mirror of CTI or an S334-2SL two-dimensional steering mirror of PI.

An implementation method based on the optical system for real-time closed-loop control of the fundus camera comprises the following steps:

A. disposing the orthogonal steering mirror group into the optical path system, the orthogonal steering mirror group comprising the first steering mirror SM1 moving in the horizontal direction and the second steering mirror SM2 moving in the vertical direction;

B. converting the fundus motion information obtained from the image of the fundus camera into the residual motion information that has been compensated by the SM1 and SM2 using the optical system;

C. manipulating the SM1 and SM2 respectively in real time to compensate for the translational motion or/and control the fundus camera to compensate for the fundus rotation by the translation control instruction and the fundus rotation control instruction using the relationship between the control parameters.

An optical system for real-time closed-loop control of a fundus camera comprises an optical path structure composed of a fundus camera, a light source, a plurality of lenses, and a dividing mirror, the fundus camera is disposed on an eyeball rotation signal compensation device; an orthogonal steering mirror group is disposed into the optical path system, the orthogonal steering mirror group comprising a first steering mirror SM1 moving in a horizontal direction and a second steering mirror SM2 moving in a vertical direction; the optical system converting fundus motion information obtained from an image of the fundus camera into residual motion information that has been compensated by the SM1 and SM2, and manipulating the SM1 and SM2 respectively in real time to compensate for a translational motion or/and control the eyeball rotation signal compensation device to compensate for a fundus rotation by a translation control instruction and a fundus rotation control instruction using a relationship between control parameters.

The relationship between the control parameters is expressed by equation (1)':

$$(x_{t+1},y_{t+1},\theta_{t+1})=(x_t,y_t,\theta_t)+g(\Delta x_t,\Delta y_t,\Delta \theta_t) \qquad (1)'$$

wherein $(x_t, y_t)$ is the translation control instruction accumulated on the first steering mirror SM1 and the second steering mirror SM2 at a current time point, $\theta_t$ is the rotation control instruction accumulated on the eyeball rotation signal compensation device at the current time point; $(\Delta x_t, \Delta y_t)$ is a residual fundus translation amount obtained from the image of the fundus camera, $\Delta \theta_t$ is a residual fundus rotation amount obtained from the image of the fundus camera; $(x_{t+1}, y_{t+1})$ is the translation control instruction that needs to be updated for the SM1 and SM2 at a next sampling time point, $\theta_{t+1}$ is the fundus/retinal rotation control instruction that needs to be updated for the eyeball rotation signal compensation device at the next sampling time point; index t represents a time sequence; g is a gain of the closed-loop control system.

The eyeball rotation signal compensation device is a rotating stage capable of rotating the fundus camera along an optical axis to optically compensate for the fundus rotation amount in real time.

The control instructions for controlling the SM1 and SM2 are configured to be sent from a personal computer or a dedicated processor connected to the fundus camera of the optical system.

The SM1 and SM2 are a 6210H biaxial scanning mirror of CTI or an S334-2SL two-dimensional steering mirror of PI.

An optical system for real-time closed-loop control of a fundus camera comprises an optical path structure composed of a fundus camera, a light source, a plurality of lenses, and a dividing mirror, and the fundus camera is disposed on an eyeball rotation signal compensation device; an orthogonal steering mirror group is disposed into the optical path system, the orthogonal steering mirror group comprising a first steering mirror SM1 moving in a horizontal direction and a second steering mirror SM2 moving in a vertical direction; the optical system obtaining a reference image from the fundus camera, importing fundus position information from outside or extracting it from a real-time video using a cross-correlation algorithm, obtaining an offset amount comprising a translation amount and a rotation amount of any current image and the reference image by calculation; and manipulating the SM1 and SM2 respectively in real time to compensate for a translational motion or/and control the eyeball rotation signal compensation device to compensate for a fundus rotation by a translation control instruction and a fundus rotation control instruction using a relationship between control parameters.

The relationship between the control parameters is expressed by equation (1)":

$$(x_{t+1},y_{t+1},\theta_{t+1})=(x_t,y_t,\theta_t)+g(\Delta x_t,\Delta y_t,\Delta \theta_t) \qquad (1)''$$

wherein $(x_t, y_t)$ is the translation control instruction accumulated on the first steering mirror SM1 and the second steering mirror SM2 at a current time point, $\theta_t$ is the rotation control instruction accumulated on the eyeball rotation signal compensation device at the current time point; $(\Delta x_t, \Delta y_t)$ is a residual fundus translation amount obtained from the image of the fundus camera, $\Delta \theta_t$ is a residual fundus rotation amount obtained from the image of the fundus camera; $(x_t+1, y_{t+1})$ is the translation control instruction that needs to be updated for the SM1 and SM2 at a next sampling time point, $\theta_{t+1}$ is the fundus/retinal rotation control instruction that needs to be updated for the eyeball rotation signal compensation device at the next sampling time point; index t represents a time sequence; g is a gain of the closed-loop control system.

The eyeball rotation signal compensation device is a mechanical device capable of compensating for an eyeball rotation signal in real time.

The control instructions for controlling the SM1 and SM2 are configured to be sent from a personal computer or a dedicated processor connected to the fundus camera of the optical system.

The SM1 and SM2 are a 6210H biaxial scanning mirror of CTI or an S334-2SL two-dimensional steering mirror of PI.

The optical system of the real-time closed-loop control of the fundus camera and implementation method therefor according to the present invention have the following beneficial effects.

1) The real-time closed-loop control of the optical system of the fundus camera according to the present invention obtains the fundus position information from the fundus image signal collected by the fundus camera, including the translation amount of the eyeball/retina obtained from the fundus image and the rotation amount of the eyeball/retina obtained from the fundus image, converts the fundus position motion information into the residual motion information which has been compensated by the steering mirrors SM1 and SM2 in a closed-loop manner, so that it is possible to determine the translation control instruction and rotation instruction that need to be updated for the steering mirrors SM1 and SM2 at the next sampling time point in a time-space domain through the translation control and rotation control instructions accumulated on the steering mirror at the current time point and the residual fundus translation and rotation amounts obtained from the fundus camera image, thereby determine a fundus/retinal motion (compensation) signal with high precision, high stability, and strong anti-interference ability for achieving the objective of closed-loop optical tracking of the fundus/retinal target using the fundus camera.

2) The present invention performs the closed-loop optical fundus tracking using the fundus camera, firstly obtains the fundus motion (compensation) signal with high precision, high stability, and strong anti-interference ability, then converts the fundus motion signal into a fundus motion (compensation) signal of a secondary optical system through an appropriate spatial transformation relationship, and controls a precise position of a light of the secondary optical system on the fundus/retina using this fundus motion (compensation) signal, and this spatially transformed fundus motion (compensation) signal also has closed-loop signal characteristics of high precision, high stability and strong anti-interference ability. The secondary optical system may be an OCT imaging system, and the position where the OCT scans the fundus is a spatial subset of an imaging position of the fundus camera; the secondary optical system may also be a fundus laser treatment system. In an embodiment of the present invention, the position where the laser strikes the fundus is a spatial subset of the imaging position of the fundus camera. The secondary optical system can also be other optical systems used in different clinical applications.

DETAILED DESCRIPTION OF THE INVENTION

Hereinafter, the technical solution of the present invention will be further described in detail in connection with the drawings and embodiments of the present invention.

Figure 1:
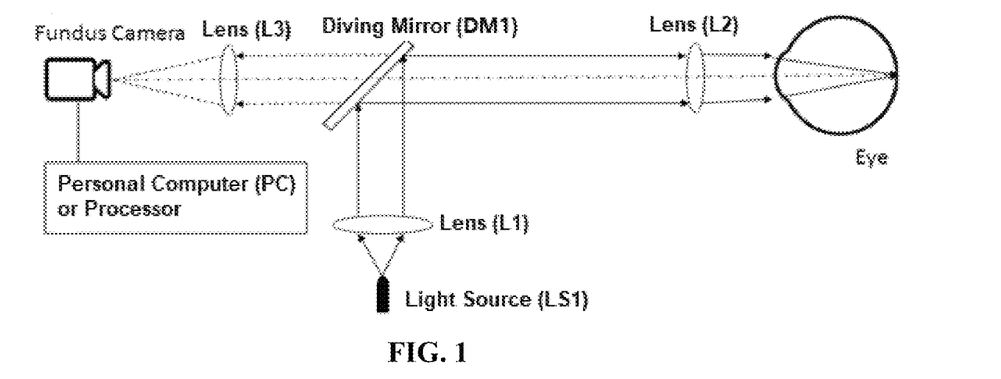
FIG. 1 is a schematic diagram of an optical system of an existing fundus camera.

FIG. 1 is a schematic diagram of an optical system of an existing fundus camera. An incident light emitted from a light source (LS) 1 is collimated by a lens L1 and reaches a dividing mirror (DM) 1. A portion of the incident light is reflected by the DM1 and enters a lens L2 to reach a fundus (Eye), namely a retina. The light reflected from the fundus transmits through the lens L2, the dividing mirror DM1, and a focusing lens L3, and is finally received by a fundus camera.

Figure 2:
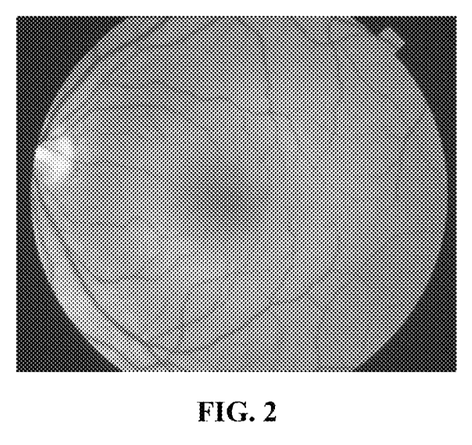
FIG. 2 is an example of a fundus image captured by an existing fundus camera.

In an embodiment of the present invention, the fundus camera may be operated independently, or may be operated by a PC or under the control of a dedicated processor. The fundus camera shown in FIG. 1 may be used to obtain an image of the fundus, as shown in FIG. 2. The image may be colorful or black-and-white.

Figure 3:
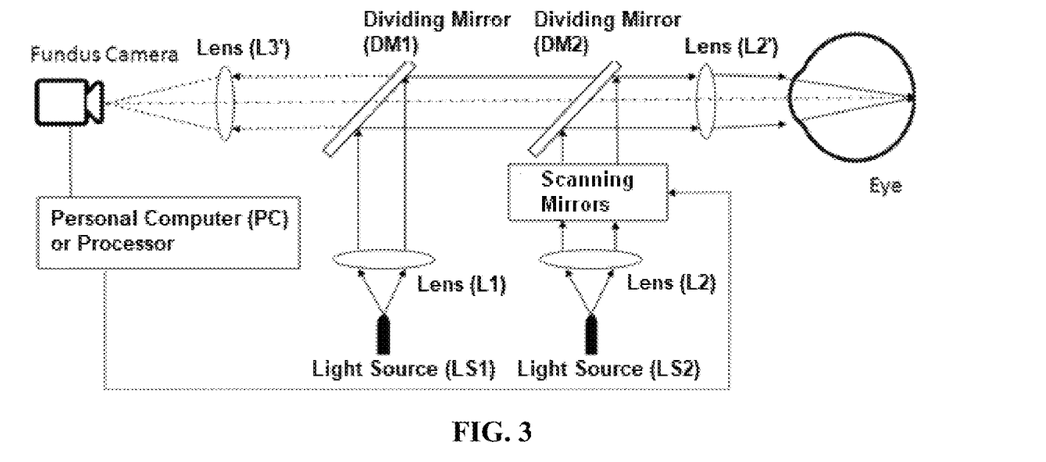
FIG. 3 is a schematic diagram of an optical system in which an existing primary fundus camera (i.e., a primary system) integrates a secondary system (i.e., an auxiliary system)

FIG. 3 is a schematic diagram of an optical system in which an existing primary fundus camera (i.e., a primary system, or known as a first system) integrates a secondary system (i.e., an auxiliary system).

In a clinical application, a secondary optical system is usually integrated into the primary fundus camera. In an embodiment of the present invention, a fundus camera with a function of closed-loop control and real-time optical tracking of fundus position is defined as the primary system; meanwhile, another optical system integrated into the primary system, with common path or non-common path, is defined as the auxiliary system.

As shown in FIG. 3, a light emitted by a light source LS2 of the auxiliary system reaches a dividing mirror DM2 after passing through optical elements of the auxiliary system, such as a lens L2 and scanning mirrors. In general, the DM2 transmits all light passing through the primary system, but reflects all light of the auxiliary system. The optical elements in the auxiliary system, such as scanning mirrors, may be controlled by the primary system or operated independently.

Figure 4:
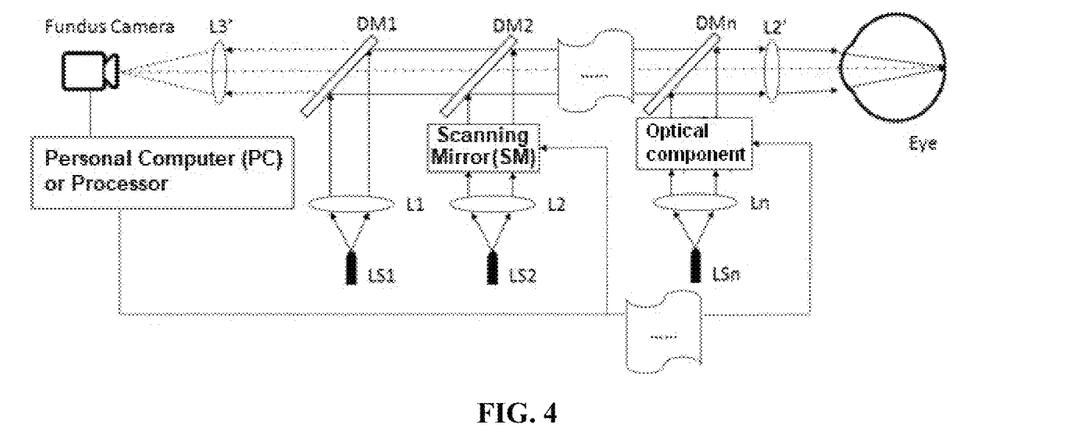
FIG. 4 is a schematic diagram of an optical system in which an existing primary fundus camera (i.e., a primary system) integrates a plurality of auxiliary systems.

FIG. 4 is a schematic diagram of an optical system in which an existing primary fundus camera (i.e., a primary system) integrates a plurality of auxiliary systems.

As shown in FIG. 4, an optical system integrates a plurality of auxiliary systems on the basis of FIG. 3. Each auxiliary system may have its own specific function, for example, one is used for OCT (Optical Coherence Tomography), and another one is used to project a focused beam onto the fundus for treatment purpose. The optical elements in each auxiliary system, such as scanning mirrors and optical component, may be controlled by the primary system or operated independently.

Figure 5:
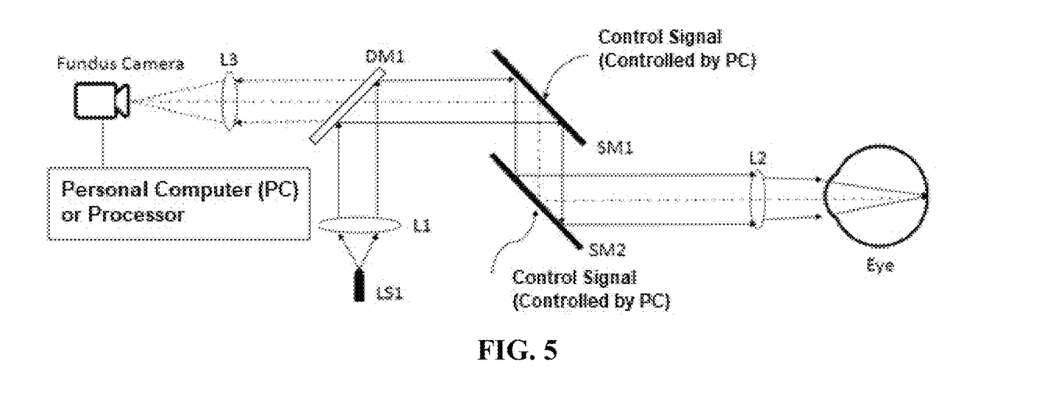
FIG. 5 is a schematic diagram of an optical system structure for real-time closed-loop control of a fundus camera according to a first embodiment of the present invention.

FIG. 5 is a schematic diagram of an optical system structure for real-time closed-loop control of a fundus camera according to a first embodiment of the invention.

In an embodiment of the present invention, by improving the above-mentioned optical system structure of the fundus camera, the improved optical system of the fundus camera has a function of real-time closed-loop control and optical tracking of the fundus position/retinal target.

As shown in FIG. 5, the optical system for real-time closed-loop control of the fundus camera disposes an orthogonal steering mirror group, which includes two orthogonally moving one-dimensional steering mirrors (SM), specifically, a first steering mirror SM1 moving in a horizontal direction and a second steering mirror SM2 moving in a vertical direction. Obviously, the steering mirrors SM1 and SM2 may move in any direction and angle in a 360-degree space, as long as the motion axes of the steering mirrors SM1 and SM2 satisfy an orthogonal relationship.

In an embodiment of the present invention, a 6210H biaxial scanning mirror of CTI (Cambridge Technology Inc) is used as the steering mirror elements.

In another embodiment of the present invention, the steering mirrors SM1 and SM2 may also be replaced with a two-dimensional steering mirror with two orthogonal motion axes. An implementable element is a S334-2SL two-dimensional steering mirror of PI (Physik Instrumente).

As shown in FIG. 5, a control instruction/signal (controlled by a PC) for controlling the steering mirrors SM1 and SM2 may be obtained from the PC or a dedicated processor.

A simple implementation is to apply a cross correlation algorithm to obtain a fundus position signal (x, y, θ) from a fundus image signal collected by the fundus camera. The specific method is to use an image previously obtained in time sequence from the fundus camera as a reference image, and cross-correlate any image obtained subsequently with the reference image to obtain a relative displacement (x, y, θ), wherein (x, y) is a translation amount of the eyeball/retina obtained from the fundus image, and θ is a rotation amount of the eyeball/retina obtained from the fundus image. A method employed in an embodiment of the present invention is to calculate (x, y, θ) by using a cross correlation algorithm. A fundus image previously obtained in time sequence is used as a reference image, for example, defined as R, and a fundus image subsequently obtained from the fundus camera at any time point is defined as $T_k$, wherein the index k (=1, 2, 3, . . . ) is the time sequence, which all occur after the reference image. The cross-correlation algorithm xcorr($T_k$, R) is performed to obtain a spatial relative relationship (x, y, θ) between $T_k$ and R. Performing the cross-correlation algorithm xcorr ($T_k$, R) may be implemented by conventional Fast Fourier Transform (FFT) or by other methods.

The above three parameters (x, y, θ) may generally describe a motion of the eyeball/fundus target relatively completely.

In the embodiment shown in FIG. 5, a closed-loop control method is disclosed. The so-called closed-loop control means that the steering mirrors SM1 and SM2 are disposed before the fundus camera as a signal detector. Before the fundus image signal enters the fundus camera, an image drift caused by the fundus motion has been compensated by the steering mirrors SM1 and SM2 in real time. Therefore, the image drift and rotation amount obtained by the fundus camera at any time point is actually residual motion information. As mentioned above, the residual motion information is still obtained from the image through the cross-correlation algorithm. In this way, in a time-space domain, the above-mentioned relationship of control parameters may be expressed in a form of equation (1):

$$(x_{t+1}, y_{t+1}, \theta_{t+1}) = (x_t, y_t, \theta_t) + g(\Delta x_t, \Delta y_t, \Delta \theta_t) \quad (1)$$

wherein ($x_t$, $y_t$) is a translation control instruction accumulated on the steering mirrors SM1 and SM2 at a current time point, $\theta_t$ is a fundus/retinal rotation control instruction accumulated at the current time point (in a certain case, such as there is only translation without rotation, and thus θt is 0); ($\Delta x_t$, $\Delta y_t$) is a residual fundus translation amount obtained from the image of the fundus camera, $\Delta \theta_t$ is a residual fundus rotation (angle) amount obtained from the image; ($x_{t+1}$, $y_{t+1}$) is the translation control instruction that needs to be updated for the steering mirrors SM1 and SM2 at a next sampling time point, and $\theta_{t+1}$ is the fundus/retinal rotation control instruction that needs to be updated (by controlling the fundus camera) at the next sampling time point. Index t represents a time sequence, and g is a gain of the closed-loop control system.

Figure 6:
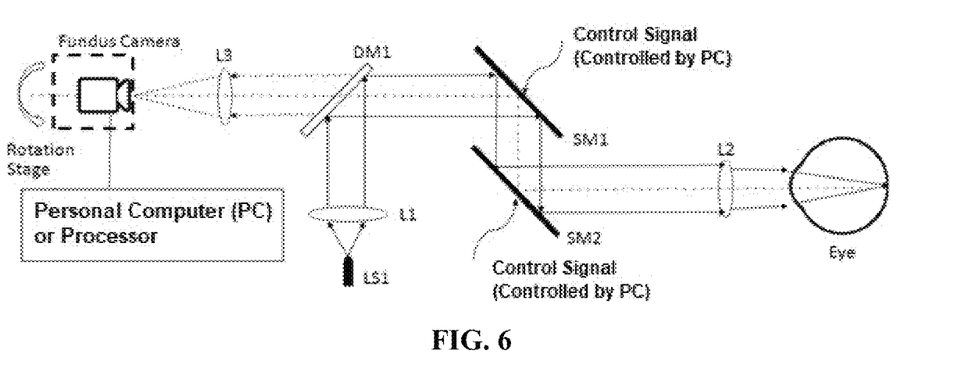
FIG. 6 is a schematic structural diagram of an optical system for real-time closed-loop control of a fundus camera according to a second embodiment of the present invention.

In the above equation (1), the eyeball/retinal rotation signal may be compensated in a digital manner, or compensated in an optical-mechanical manner as shown in FIG. 6 below.

FIG. 6 is a schematic structural diagram of an optical system for real-time closed-loop control of a fundus camera according to a second embodiment of the present invention.

In the optical-mechanical compensation, one method is to mount the fundus camera on an eyeball rotation signal compensation device, such as a rotation stage, so that the fundus camera may rotate along an optical axis for real-time optical compensation of the fundus rotation amount. In this case, $\theta_t$ is the rotation control instruction accumulated on the rotating stage at the current time point, $\Delta \theta_t$ is the residual fundus rotation amount obtained from the fundus camera image, and $\theta_{t+1}$ is the rotation control instruction that needs to be updated for the rotating stage at the next sampling time point. In this embodiment, the remaining of the optical path structure is the same as that shown in FIG. 5.

As shown in FIG. 6, the optical system for real-time closed-loop control of the fundus camera also provides another eyeball rotation signal compensation device, such as a mechanical device for real-time compensation of the eyeball rotation signal. In this embodiment, a two-dimensional camera for imaging is mounted on a rotation stage (see the dashed rectangular box), and the rotating axis of the rotation stage is consistent with the optical axis of the optical system.

As shown in equation (1), the method of obtaining the fundus position information from the camera image usually employs a cross-correlation method. The method is to firstly select a reference image, import the fundus position information from an external file or extract it from a real-time video; in the following time sequence, calculate an offset amount including a translation amount and a rotation amount of any future current image and this reference image, such as ($\Delta x_t$, $\Delta y_t$, $\Delta \theta_t$) in equation (1).

Figure 7:
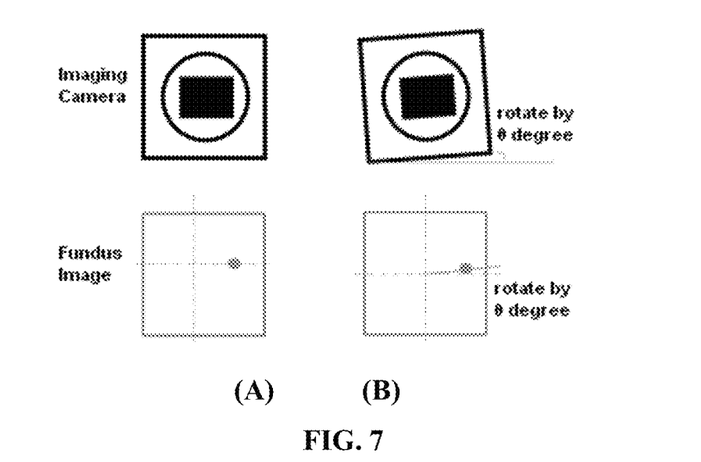
FIG. 7 is a schematic diagram of a rotating imaging camera for compensating rotational motion of a fundus according to the present invention.

FIG. 7 is a schematic diagram of a rotating imaging camera for compensating rotational motion of a fundus according to the present invention. The fundus rotation may be caused by many factors, including eyeball rotation, head rotation or other reasons, but for a fundus imaging system, the final result is a rotation of the fundus image. Therefore, here are collectively referred to as fundus rotation.

As shown in FIG. 7, the lower part of FIG. 7A is the reference image, and the upper part is the position of the imaging camera. The lower part of FIG. 7B shows due to the rotation of the fundus, the image obtained by the fundus camera also rotates, such as "rotate by 0 degree" in the figure.

The cross-correlation algorithm obtains the rotation angle θ from the above images in FIGS. 7A and 7B in a closed-loop manner from equation (1). Then, the angle θ may be sent to the rotation stage that controls the fundus (imaging) camera, to make a photosensitive surface of the imaging camera also rotate by θ degree to compensate for the rotation amount θ of the fundus. An equivalent result of the rotation compensation is to restore the image obtained by the camera to the position of the lower image in FIG. 7A.

Figure 8:
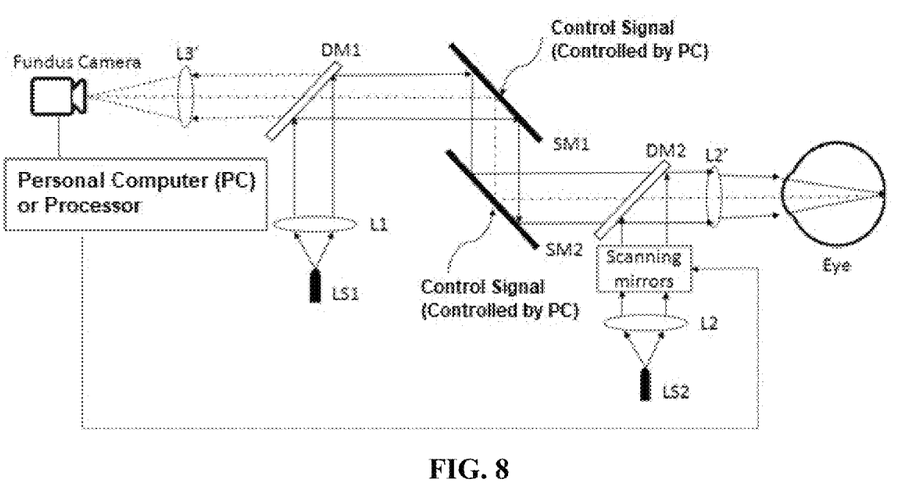
FIG. 8 is a schematic diagram of an optical system in which a primary fundus camera imaging system is used to implement closed-loop control of a secondary system according to the first embodiment of the present invention.

FIG. 8 is a schematic diagram of an optical system in which a primary fundus camera imaging system is used to implement closed-loop control of a secondary system according to the first embodiment of the present invention.

As shown in FIG. 8, a closed-loop control fundus tracking signal of the primary system is used to drive one or more similar optical-mechanical devices of the auxiliary system, so that the auxiliary system may also achieve the purpose of tracking the fundus position.

As shown in FIG. 8, the closed-loop control of the primary fundus camera imaging system still employs the relationship of equation (1). In order to achieve the purpose that the auxiliary system may also track the eyeball motion, the eyeball motion signal (x, y, θ) obtained by the primary imaging system needs to be converted to the scanning mirrors or tracking mirrors of the auxiliary system. The tracking mirrors of the primary imaging system, namely steering mirrors SM1 and SM2, are used for the tracking within the primary imaging system, and the scanning mirrors or tracking mirrors of the auxiliary system is used for the optical tracking within the auxiliary system.

The spatial transformation relationship f(x, y, θ; x', y', θ') between the tracking mirrors SM1 and SM2 of the primary imaging system and the scanning mirrors of the auxiliary system is implemented by system calibration. As such, at any sampling time point, the control signals sent to the tracking mirrors of the auxiliary system according to equation (1) have the following relationship:

$$(x'_{t+1}, y'_{t+1}, \theta'_{t+1}) = f(x, y, \theta; x', y', \theta')(x_{t+1}, y_{t+1}, \theta_{t+1}) \quad (2)$$

The result of the above equation (2) is used to adjust the position of the scanning mirrors of the auxiliary system to implement the real-time tracking of the target by the auxiliary system. However, this group of signals does not include the unique functions of the scanning mirrors of the auxiliary system used by itself, such as OCT scanning of the fundus.

Figure 9:
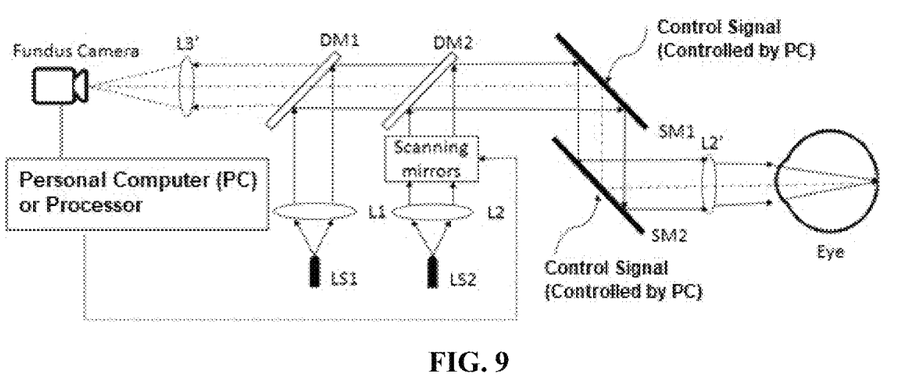
FIG. 9 is a schematic diagram of an optical system in which a primary fundus camera imaging system is used to implement closed-loop control of a secondary system according to the second embodiment of the present invention.

FIG. 9 is a schematic diagram of an optical system in which a primary fundus camera imaging system is used to implement closed-loop control of a secondary system according to the second embodiment of the present invention.

As shown in FIG. 9, it is another embodiment of the present invention in which the optical tracking closed-loop control of the primary imaging system is used to drive the tracking of one or more auxiliary imaging systems.

As shown in FIG. 9, the tracking mirrors of the primary imaging system, namely steering mirrors SM1 and SM2, are shared by all auxiliary systems. In other words, after the real-time compensation of the SM1 and SM2, the eyeball motion signal reaching the auxiliary system has also been compensated. If the auxiliary system is an imaging system, such as an OCT, the real-time image of the OCT has been stabilized by the SM1 and SM2.

In FIG. 9, the scanning mirrors of the auxiliary system are only used for its own purposes, such as B-scan and C-scan of the OCT, or for navigating the spatial position of the focused laser beam projected to the fundus. However, there may also be some special reasons involved in the design of the optical system. The primary system and the auxiliary system have different optical magnifications, spatial offsets amount and other reasons. As such, in order for the auxiliary system to accurately track the fundus position, it is still necessary to use a spatial transformation relationship such as equation (2) to convert the eyeball motion information of the primary system to the scanning mirrors of the auxiliary system to implement the optical tracking of the auxiliary system.

Figure 10:
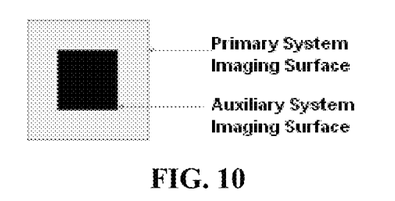
FIG. 10 is a schematic diagram of a correspondence relationship between imaging spaces of the primary and auxiliary systems according to the present invention.

FIG. 10 is a schematic diagram of a correspondence relationship between imaging spaces of the primary and auxiliary systems according to the present invention.

As shown in FIG. 10, it is assumed that the size of the imaging surface of the primary optical system is exactly twice the size of the imaging surface of the auxiliary system, and the imaging center positions of the two systems are consistent with each other. This is very common in clinical practice, for example, the auxiliary system "digging out" a local area from the primary system for optical/digital magnification, or other forms of imaging. Then, when using the spatial transformation relation of equation (2), it is easy to obtain:

$$x'_{t+1} = x_{t+1}/2 \quad (3)$$

$$y'_{t+1} = y_{t+1}/2 \quad (4)$$

$$\theta'_{t+1} = \theta_{t+1} \quad (5)$$

Obviously, the spatial mapping relationship between the primary system and the auxiliary system in the above equations (3), (4), and (5) may also have other forms than FIG. 10, then equations (3)-(5) obtained from equation (2) have different results.

Once the design of the optical system is determined, this certain relationship may generally be obtained by one-time calibration measurement and calculation.

The foregoing descriptions are only preferred embodiments of the present invention, and are not used to limit the protection scope of the present invention.

The invention claimed is:

1. An optical system for real-time closed-loop control of a fundus camera, comprising an optical path structure composed of a fundus camera, a light source, a plurality of lenses, and a dividing mirror, and characterized by further comprising an orthogonal steering mirror group, the orthogonal steering mirror group comprising a first steering mirror SM1 moving in a horizontal direction and a second steering mirror SM2 moving in a vertical direction; the optical system is arranged to convert fundus motion information obtained from an image of the fundus camera into residual motion information that has been compensated by the SM1 and SM2, and to manipulate the SM1 and SM2 respectively in real time to compensate for a translational motion or/and control the fundus camera to compensate for a fundus rotation by a translation control instruction and a fundus rotation control instruction using a relationship between control parameters; characterized in that the relationship between the control parameters is expressed by equation (1):

$$(x_{t+1}, y_{t+1}, \theta_{t+1}) = (x_t, y_t, \theta_t) + g(\Delta x_t, \Delta y_t, \Delta \theta_t) \quad (1)$$

wherein $(x_t, y_t)$ is the translation control instruction accumulated on the first steering mirror SM1 and the second steering mirror SM2 at a current time point, $\theta_t$ is the fundus/retinal rotation control instruction accumulated at the current time point; $(\Delta x_t, \Delta y_t)$ is a residual fundus translation amount obtained from the image of the fundus camera, $\Delta \theta_t$ is a residual fundus rotation amount obtained from the image; $(\Delta x_{t+1}, \Delta y_{t+1})$ is the translation control instruction that needs to be updated for the SM1 and SM2 at a next sampling time point, $\theta_{t+1}$ is the fundus/retinal rotation control instruction that needs to be updated at the next sampling time point; index t represents a time sequence; g is a gain of the closed-loop control system.

2. The optical system for real-time closed-loop control of the fundus camera according to claim 1, characterized in that the control instructions for controlling the SM1 and SM2 are configured to be sent from a personal computer or a dedicated processor connected to the fundus camera of the optical system.

3. The optical system for real-time closed-loop control of the fundus camera according to claim 1, characterized in that the SM1 and SM2 are a 6210H biaxial scanning mirror of CTI or an S334-2SL two-dimensional steering mirror of PI.

4. An optical system for real-time closed-loop control of a fundus camera, comprising an optical path structure composed of a fundus camera, a light source, a plurality of lenses, and a dividing mirror, and characterized by the fundus camera is disposed on an eyeball rotation signal compensation device; an orthogonal steering mirror group is disposed into the optical path system, the orthogonal steering mirror group comprising a first steering mirror SM1 moving in a horizontal direction and a second steering mirror SM2 moving in a vertical direction; the optical system is arranged to convert fundus motion information obtained from an image of the fundus camera into residual motion information that has been compensated by the SM1 and SM2, and to manipulate the SM1 and SM2 respectively in real time to compensate for a translational motion or/and control the eyeball rotation signal compensation device to compensate for a fundus rotation by a translation control instruction and a fundus rotation control instruction using a relationship between control parameters-; characterized in that the relationship between the control parameters is expressed by equation (1)':

$$(x_{t+1}, y_{t+1}, \theta_{t+1}) = (x_t, y_t, \theta_t) + g(\Delta x_t, \Delta y_t, \Delta \theta_t) \quad (1)'$$

wherein $(x_t, y_t)$ is the translation control instruction accumulated on the first steering mirror SM1 and the second steering mirror SM2 at a current time point, $\theta_t$ is the rotation control instruction accumulated on the eyeball rotation signal compensation device at the current time point; $(\Delta x_t, \Delta y_t)$ is a residual fundus translation amount obtained from the image of the fundus camera, $\Delta\theta_t$ is a residual fundus rotation amount obtained from the image of the fundus camera; $(\Delta x_{t+1}, \Delta y_{t+1})$ is the translation control instruction that needs to be updated for the SM1 and SM2 at a next sampling time point, $\theta_{t+1}$ is the fundus/retinal rotation control instruction that needs to be updated for the eyeball rotation signal compensation device at the next sampling time point; index t represents a time sequence; g is a gain of the closed-loop control system.

5. The optical system for real-time closed-loop control of the fundus camera according to claim 4, characterized in that the eyeball rotation signal compensation device is a rotating stage capable of rotating the fundus camera along an optical axis to optically compensate for the fundus rotation amount in real time.

6. The optical system for real-time closed-loop control of the fundus camera according to claim 4, characterized in that the control instructions for controlling the SM1 and SM2 are configured to be sent from a personal computer or a dedicated processor connected to the fundus camera of the optical system.

7. The optical system for real-time closed-loop control of the fundus camera according to claim 4, characterized in that the SM1 and SM2 are a 6210H biaxial scanning mirror of CTI or an S334-2SL two-dimensional steering mirror of PI.

8. An optical system for real-time closed-loop control of a fundus camera, comprising an optical path structure composed of a fundus camera, a light source, a plurality of lenses, and a dividing mirror, and characterized by the fundus camera is disposed on an eyeball rotation signal compensation device; an orthogonal steering mirror group is disposed into the optical path system, the orthogonal steering mirror group comprising a first steering mirror SM1 moving in a horizontal direction and a second steering mirror SM2 moving in a vertical direction; the optical system is arranged to obtain a reference image from the fundus camera, to import fundus position information from outside or extract it from a real-time video using a cross-correlation algorithm, to obtain an offset amount comprising a translation amount and a rotation amount of any current image and the reference image by calculation; and to manipulate the SM1 and SM2 respectively in real time to compensate for a translational motion or/and control the eyeball rotation signal compensation device to compensate for a fundus rotation by a translation control instruction and a fundus rotation control instruction using a relationship between control parameters; characterized in that the relationship between the control parameters is expressed by equation (1)";

$$(x_{t+1}, y_{t+1}, \theta_{t+1}) = (x_t, y_t, \theta_t) + g(\Delta x_t, \Delta y_t, \Delta\theta_t) \qquad (1)''$$

wherein $(x_t, y_t)$ is the translation control instruction accumulated on the first steering mirror SM1 and the second steering mirror SM2 at a current time point, $\theta_t$ is the rotation control instruction accumulated on the eyeball rotation signal compensation device at the current time point; $(\Delta x_t, \Delta y_t)$ is a residual fundus translation amount obtained from the image of the fundus camera, $\Delta\theta_t$ is a residual fundus rotation amount obtained from the image of the fundus camera; $(\Delta x_{t+1}, \Delta y_{t+1})$ is the translation control instruction that needs to be updated for the SM1 and SM2 at a next sampling time point, $\theta_{t+1}$ is the fundus/retinal rotation control instruction that needs to be updated for the eyeball rotation signal compensation device at the next sampling time point; index t represents a time sequence; g is a gain of the closed-loop control system.

9. The optical system for real-time closed-loop control of the fundus camera according to claim 8, characterized in that the eyeball rotation signal compensation device is a mechanical device capable of compensating for an eyeball rotation signal in real time.

10. The optical system for real-time closed-loop control of the fundus camera according to claim 8, characterized in that the control instructions for controlling the SM1 and SM2 are configured to be sent from a personal computer or a dedicated processor connected to the fundus camera of the optical system.

11. The optical system for real-time closed-loop control of the fundus camera according to claim 8, characterized in that the SM1 and SM2 are a 6210H biaxial scanning mirror of CTI or an S334-2SL two-dimensional steering mirror of PI.

* * * * *